United States Patent [19]
Halperin et al.

[11] Patent Number: 5,556,871
[45] Date of Patent: Sep. 17, 1996

[54] METHOD FOR TREATING EPITHELIAL PRECANCEROUS LESIONS WITH TOPICAL INIDAZOLES

[75] Inventors: Jose Halperin, Brookline; Carlo Brugnara, Newton Highlands; Harley Haynes, Bedford, all of Mass.

[73] Assignee: President & Fellows of Harvard College, Cambridge, Mass.

[21] Appl. No.: 427,485

[22] Filed: Apr. 24, 1995

[51] Int. Cl.⁶ .................................................. A61K 31/415
[52] U.S. Cl. ..................... 514/396; 514/252; 514/399
[58] Field of Search .................................. 514/252, 396, 514/399

[56] References Cited

U.S. PATENT DOCUMENTS

| | | |
|---|---|---|
| 3,678,030 | 7/1972 | Yamazaki et al. . |
| 3,901,908 | 8/1975 | Fitzi et al. . |
| 3,940,486 | 2/1976 | Fitzi . |
| 3,965,112 | 6/1976 | White et al. ............... 260/309 |
| 4,073,922 | 2/1978 | Wyburn-Mason . |
| 4,119,723 | 10/1978 | Wyburn-Mason . |
| 4,218,449 | 8/1980 | Wyburn-Mason . |
| 4,491,588 | 1/1985 | Rosenburg et al. . |
| 4,569,935 | 2/1986 | Rosenberg et al. . |
| 4,657,925 | 4/1987 | Horn . |
| 4,758,580 | 7/1988 | Numasaki et al. . |
| 4,837,333 | 6/1989 | Manley et al. . |
| 4,886,818 | 12/1989 | Numasaki et al. . |
| 4,916,118 | 4/1990 | Fidler et al. . |
| 4,942,162 | 7/1990 | Rosenburg et al. . |
| 5,001,134 | 3/1991 | Gerard et al. . |
| 5,023,090 | 6/1991 | Levin . |
| 5,057,530 | 10/1991 | Barner et al. . |
| 5,059,590 | 10/1991 | Ueda et al. . |
| 5,132,315 | 7/1992 | Kohn et al. . |
| 5,273,992 | 12/1993 | Brugnara et al. ............ 31/415 |
| 5,326,790 | 7/1994 | Thornfeldt . |
| 5,358,959 | 10/1994 | Halperin et al. . |
| 5,385,938 | 1/1995 | Yu et al. . |
| 5,389,677 | 2/1995 | Yu et al. . |

FOREIGN PATENT DOCUMENTS

| | | |
|---|---|---|
| 1004029 | 9/1992 | Belgium . |
| 2273873 | 12/1992 | United Kingdom . |
| WO91/19707 | 12/1991 | WIPO . |
| WO94/18967 | 9/1994 | WIPO . |
| WO94/18968 | 9/1994 | WIPO . |

OTHER PUBLICATIONS

Rosenberg, E. W. et al., Improvement of Psoriasis of the Scalp with Ketaconazole; Arch. Dermatol, Jun. 1982; 370–371.
Shelnitz, L. S. et al., Etretinate Therapy for Generalized Pustular Psoriasis in Children; Arch. Dermatol. Feb. 1987; pp. 230–233.
Lee, R. E. et al., Interleukin 2 and Psoriasis; Arch.Dermatol. v.124, Dec. 1988; pp. 1811–1815.
Going, S., The Treatment of Psoriasis; The Practitioner, Jul. 1988, v. 232; pp. 824–827.
Al–Ghamdi, F. et al., Dramatic Effect of Cyclosporin in Generalized Pustular Psoriasis–The Effective Dose; Saudi Med.J.v.13 No5 1982.
Fisher, J. et al., Therapeutic Failures with Miconazole; Antimicrobial Agents and Chemotherapy; Jun. 1978; pp. 965–968.
Dixon, B. S. et al., Histidine Regulation of Cyclic AMP Metabolism in Cutlured Renal Epithelial LLC–PK1 Cells; J. Biol. Chem., v. 265, No. 2, Jan. 15, 1990; pp. 760–766.
Coskey, R. J., Dermatologic Therapy: 1993; J. of the American Academy of Dermatology; Nov. 1994, pp. 764–774.
Heel, R. C. et al., Miconazole: A Preliminary Review of its Therapeutic Efficacy in Systemic Fungal Infections, (1980), 7–30, Drugs 19.
Ritter, W. et al., Pharmacokinetic Fundamentals of Vaginal Treatment with Clotrimazole; (1982); 37–42; Chemotherapy 28.
Ritter, W.; Pharmacokinetic fundamentals of vaginal treatment w/clotrimazole; Am J. Obstet. Gynecol., 152:945–947 (1985).
Duhm, B. et al., The pharmacokinetics of clotrimazole 14C; (Jul. 1974); 13–16; Postgraduate Medical Journal 50.
W. Wouters et al.; Effects of Liarozole, a New Antitumoral Compound, on Retinoic Acid–induced Inhibition of Cell Growth and on Retinoic Acid Metabolism in MCF–7 Human Breast Cancer Cells; May 15, 1992; pp. 2841–2846; Cancer Research 52.
A. Najid and M. Ratinaud; Comparative Studies of Steroidogenesis Inhibitors (Econazole, Ketoconazole) on Human Breast Cancer MCF–7 Cell Proliferation by Growth Experiments, Thymidine Incorporation and Flow Cytometric DNA Analysis; 1991; pp. 385–390; Tumori 77.
N. Burres et al.; Antitumor Activity and Biochemical Effects of Topsentin; 1991; pp. 745–751; Biochemical Pharmacology, vol. 42.
T. Nordstrom et al.; Mitosis–Arresting Effect of the Calcium Channel Inhibitor SK&F 96365 on Human Leukemia Cells; 1992; pp. 487–494; Experimental Cell Research, vol. 202.
A. Galeano et al.; Antitumor Activity of Some Ruthenium Derivatives in Human Colon Cancer Cell Lines in vitro; 1992; pp. 821–824; Drug Res., vol. 42.
Sawyer, P. et al., Clotrimazole: A Review of its Antifungal Activity and Therapeutic Efficacy; Drugs 9:424–447; (1975).
Ohnishi, S. T. et al, Inhibition of the In Vitro Formation of Dense Cells and of Irreversibly Sickled Cells by Charybdotoxin, A Specific Inhibitor of Calcium–Activated Potassium Efflux; 199–203; Biochemica et Biophysica Acta 1010 (1989).

(List continued on next page.)

Primary Examiner—Rebecca Cook
Attorney, Agent, or Firm—Wolf, Greenfield & Sacks P.C.

[57] ABSTRACT

A method of treating epithelial precancerous lesions is provided. The method involves the administration of certain imidazoles to an epithelial precancerous lesion. The preferred imidazoles are clotrimazole, miconazole, econazole and ketoconazole. The method of the invention is especially useful in treating actinic keratosis.

19 Claims, No Drawings

OTHER PUBLICATIONS

Wolff, D. et al, Charybdotoxin Blocks with High Affinity the Ca–Activated K+ Channel of HB A and Hb S Red Cells: Individual Differences in the Number of Channels; J. Membrane Biol. 106, 243–252 (1988).

Brugnara, C. et al., Ca2+–activated K+ Transport in Erythrocytes J. Biol. Chem.; 1993; 8760–8768.

De Franceschi, L.; Treatment with Oral Clotrimazole Blocks Ca2+–activated K+ Transport and Reverses Erythrocyte Dehydration in Transgenic SAD Mice; J. Clin. Invest. 93: 1670–1676; Apr. 1994.

Brugnara, C. et al., Inhibition of Ca2+–dependent K+ Transport and Cell Dehydration in Sickle Erythrocytes by Clotrimazole and Other Imidazole Derivatives; J.Clin.Invest. 92:520–526; Jul. '93.

Muhktar, H. et al., Clotrimazole, an Inhibitor of Epidermal Benzo(a)pyrene Metabolism and DNA Binding and Carcinogenicity of the Hydrocarbon; Cancer Res., 44:4283–4240, Oct. 1984.

Forgue–Lafitte, M. E. et al., Effects of Ketoconazole on the Proliferation and Cell Cycle of Human Cancer Cell Lines; Cancer Res Res., 52:6827–6831, Dec. 15, 1992.

Tzanakakis, G. et al., Inhibition of Hepatic Metastasis From a Human Pancreatic Andenocarcinoma (RWP–2) in the Nude Mouse by Prostacyclin, Forskolin and Ketoconazole, Cancer 65:446–451, 1990.

Calmodulin Antagonists in Psoriasis; SCRIP No. 1797, Feb. 23, 1993 p. 23.

F. Delbarre, On the Possible Anti–Rheumatic Effects Immuno–effector of Imidazole Derivatives (levamisole, clortrimazole, niridazole), Biomedicine, 1977, 27, 97–98.

Knud Lund–Olesen, Clotrimzaole, Plasma Cortisol and Rheumatoid Arthritis; Current Therapeutic Research, vol. 21, No. 5, May, 1977 704–706.

W. Dennison et al., A Double Blind Placebo Controlled Trial of Low Dose Clotrimazole in Rheumatoid Arthritis; The Journal of Rheumatology, 1990; 17:8; 1003–1007.

Wojtulewski et al., Clotrimazole in rheumatoid Arthritis; Annals of the Rheumatic Diseases; 1980, 39, 469–572.

Chemical Abstracts : CA 101:183620 (1984).

Chemical Abstracts : CA 116: 187584x (1992).

Chemical Abstracts : CA 106:209231c (1987).

Nardone, P. et al., Ketoconazole: A thromboxane Synthetase and 5–Lipoxygenase Inhibitor with Antimetastatic Activity in B16–F10 Melanoma: J. Surgical Res., 44: 425–429 (1988).

Society of General Physiologists 48th Annual Symposium; Ion Channels and Genetic Diseases; Sep. 8, 1994.

MacNeil et al., Antiproliferative effects on keratinocytes of a range of clinically used drugs with calmodulin antagonist activity, Br. J. Dermatology, v. 128, pp. 143–150 (1993).

METHOD FOR TREATING EPITHELIAL PRECANCEROUS LESIONS WITH TOPICAL INIDAZOLES

BACKGROUND

Precancerous skin lesions of keratinocytes are those areas of skin in which tissue shows the tendency to develop into cancer, although the tissue in its present state is not a cancer. Epithelial precancerous lesions include actinic keratosis (also called solar keratosis or senile keratosis), hypertrophic actinic keratosis, Bowenoid actinic keratosis, arsenical keratosis, hydrocarbon keratosis, thermal keratosis, radiation keratosis, chronic scar keratosis, viral keratosis, Bowen's disease, erythroplaquia of queyrat, oral erythroplaquia, leukoplakia, and intraepidermal epithelialoma.

Actinic keratosis is the most common epithelial precancerous lesion among fair skinned individuals. It is usually present as lesions on the skin which may or may not be visually detectable. The size and shape of the lesions varies. It is a photosensitive disorder and may be aggravated by exposure to sunlight. If left untreated, the lesions may proceed to form atypical squamous cells, one example of which is Bowenold actinic keratosis.

Bowenoid actinic keratosis is another form of an epithelial precancerous lesion. In some cases, the lesions may develop into an invasive form of squamous cell carcinoma and may pose a significant threat of metastasis. Actinic keratosis is characterized by an inflammatory infiltration of lymphocytes, histocytes and a variable number of plasma cells. It further is characterized by proliferation of keratinocytes. There also is evidence that actinic keratosis has mutations of the P53 and H-RAS oncogenes that probably are related to the malignant potential of the lesions.

Actinic keratosis is often treated with topical application of 5-fluorouracil or with a cryosurgery technique utilizing liquid nitrogen. Other treatment approaches include the topical or parenteral application of cytostatic agents and the topical application of corticosteroids. However, these treatments often produce side effects which prevents their use as chronic treatments.

Certain imidazoles such as clotrimazoles are synthetic anti-fungal agents that are used both topically and systemically. Indications for their use include ring worm, tinea versicolor and mucocutaneous candidiasis. These compounds are believed to act by inhibiting ergosterol synthesis in the fungal cell wall, and when given topically, may cause direct damage to the fungal cytoplasmic membrane.

Various imidazoles have been suggested as treatments for certain cellular disorders. For instance, ketoconazole appears to inhibit in high doses testicular and adrenal synthesis of steroid hormones, including testosterone. The ability of ketoconazole to block steroid synthesis is believed to be effective in treating some prostate cancers because proliferation of certain prostate cancer cells is highly dependent upon testosterone. Likewise, econazole has been shown to be effective in the treatment of breast cancer, by inhibiting steroidogenesis.

Imidazoles have also been found to be useful in the prevention of sickle cell dehydration by inhibiting potassium loss via the gardos channel in erythrocytes. The imidazoles found to be useful in the treatment of sickle cell dehydration include clotrimazole, miconazole, econazole, butoconazole, oxyconazole and solconazole. (U.S. Pat. No. 5,273,992). In further investigations Brugnara et al. found that metabolites of antimycotic imidazoles without the imidazole group were also effective in the prevention of sickle cell dehydration. (U.S. Ser. No. 08/307,874).

Previous studies by the authors have shown that clotrimazole inhibits cellular proliferation of normal endothelial and vascular smooth muscle cell lines in vitro. U.S. Pat. No. 5,358,959 relates to the ability of imidazoles to inhibit endothelial cell and vascular smooth muscle cell proliferation in the treatment of atroclerosis by inhibiting re-stenosis. U.S. Pat. No. 5,512,591 relates to the use of certain imidazoles to inhibit vascular smooth muscle cell proliferation in order to inhibit angiogenesis. The use of imidazoles to inhibit angiogenesis was suggested for treating conditions characterized by abnormal neovascularization.

In U.S. patent application Ser. No. 08/018,828, it was proposed that the proliferation of certain cancer cells can be inhibited by certain imidizoles. This hypothesis is based upon data showing the inhibition of proliferation of cancer cell lines in vitro and in vivo in animals.

It was postulated that the mechanism by which such imidazoles inhibit the proliferation of smooth muscle cells, endothelial cells and cancer cells is through the regulation of cellular calcium levels, rather than by an inhibition of steroidogenesis (the mechanism suggested for the antiproliferative effect of econazole and ketoconazole on breast and prostate cancer cells, respectively). At the cellular level, clotrimazole appears to inhibit both calcium activated potassium channels and calcium channels in the plasma membrane as well as depleting intracellular stores of calcium.

Psoriasis is an inflamatory disorder of the skin characterized by the presence of skin lesions. Psoriasis is considered to be a genetic papulosquamous skin disorder. Papulosquamous skin lesions may be associated with a variety of disorders such as, Reiter's disease. However, they are distinct from photosensitive disorders. Psoriasis has been treated with drugs which act as calmodulin antagonists, including miconazole. Calmodulin antagonists provide an increase in cellular caclium.

The imidizoles discussed above have not been shown or used previously to inhibit the proliferation of epithelial cells. They also have not been shown or used to inhibit the proliferation of precancerous cells having transformed oncogenes, such as mutations of the P53 and H-RAS oncogenes. They further have not been shown to affect the inflammatory infiltration of lymphocytes, histocytes and the like. All of the foregoing are features of actinic keratosis, and epithelial precancerous lesions. Likewise, the use of such imidazoles for the treatment of actinic keratosis thus has not been shown or suggested.

SUMMARY OF THE INVENTION

The present invention provides methods for treating an epithelial precancerous lesion. It has been discovered that certain imidazoles can inhibit the growth of epithelial precancerous lesions. In one embodiment of the invention, prefered compounds are imidazoles wherein the imidazole is selected from the group consisting of clotrimazole, ketoconazole, econazole and miconazole.

The present invention thus pertains to methods of treating a subject having an epithelial precancerous lesion by administering to subjects in need of such treatment an effective amount of the foregoing compounds. Preferably the subject treated by the methods of the invention has actinic keratosis.

DETAILED DESCRIPTION OF THE INVENTION

The invention involves methods for inhibiting epithelial precancerous lesions. The present invention involves the unexpected finding that certain imidazoles can inhibit epithelial cell proliferation, and particularly can inhibit precancerous epithelial cell proliferation associated with actinic keratosis.

An epithelial precancerous lesion is a skin lesion which has a propensity to develop into a cancerous condition. The symptoms of epithelial precancerous lesions include skin-colored or red-brown macule or papule with dry adherent scales. These lesions include actinic keratosis, also called solar keratosis or senile keratosis, hypertrophic actinic keratosis, Bowenoid actinic keratosis, arsenical keratosis, hydrocarbon keratosis, thermal keratosis, radiation keratosis, chronic scar keratosis, viral keratosis, Bowen's disease, erythroplaquia of queyrat, oral erythroplaquia, leukoplakia, and intraepidermal epithelialoma. Epithelial precancerous skin lesions also arise from other proliferative skin disorders such as hemangiomas, keloids, eczema and papilloma virus infections producing verruca vulbaris, verruca plantaris and verruca planar.

Actinic keratosis is the most common type of epithelial precancerous lesion. It generally develops as a response to exposure to sunlight. Patients with actinic keratosis are typically fair skinned and elderly. However actinic keratosis may be present in young people, especially those who have undergone renal transplantation or are immunocompromised.

The imidazoles according to the invention include clotrimazole, econazole, miconazole, and ketoconazole. These compounds have the following chemical structures:

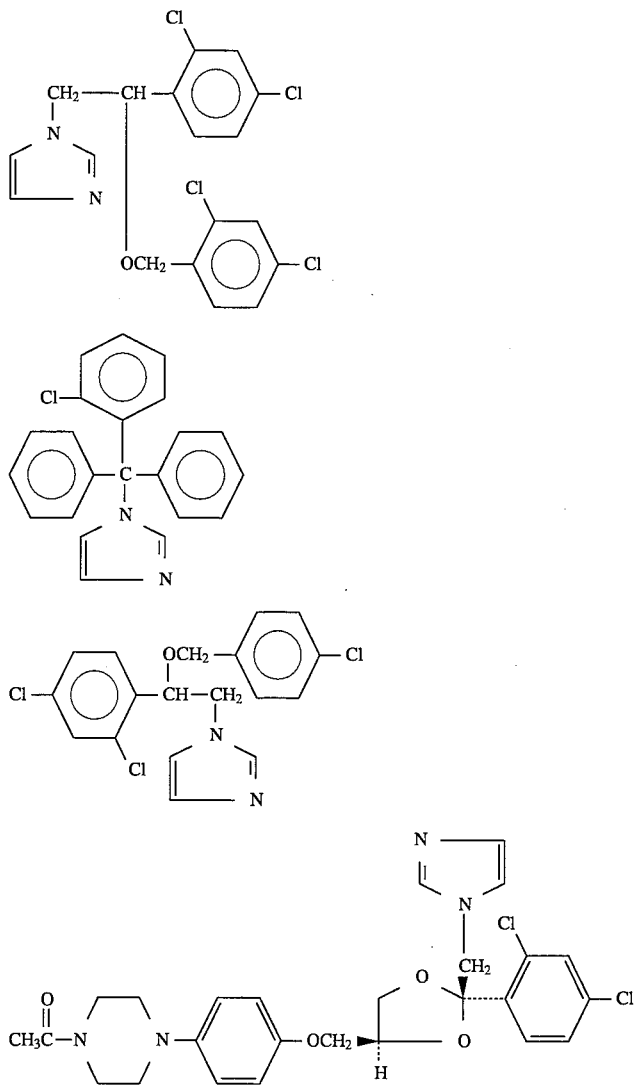

As used herein the foregoing imidazoles include their salts, such as econazole nitrate and miconazole nitrate. The imidazoles of the invention should be administered in a pharmaceutical preparation for treating an epithelial precancerous lesion. The pharmaceutical preparation is a pharmaceutically acceptable one of the imidazoles described above and lactic acid. Preferably the preparation is 3% clotrimazole and 5% lactic acid. Lactic acid, or 2-hydroxypropanoic acid has the following structural formula:

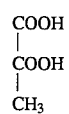

When administered the formulations of the invention are applied in pharmaceutically acceptable amounts. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicyclic, p-toluene sulphonic, tartaric, citric, methane sulphonic, formic, malonic, succinic, naphthalene-2-sulphonic, and benzene sulphonic. Also, pharmaceutically acceptable salts can be prepared as alkyline metal or alkyline earth salts, such as sodium, potassium or calcium salts of the carboxylic acid group. Thus, the present invention involves the use of pharmaceutical formulations which comprise certain imidazoles, together with one or more pharmaceutically acceptable carriers and optionally other therapeutic ingredients.

The term "pharmaceutically-acceptable carrier" as used herein means one or more compatible solid or liquid filler, dilutants or encapsulating substances which are suitable for administration to a human or other animal. The term "carrier" denotes an organic or inorganic ingredient, natural or synthetic, with which the active ingredient is combined to facilitate the application. The components of the pharmaceutical compositions also are capable of being comingled with the molecules of the present invention, and with each other, in a manner such that there is no interaction which would substantially impair the desired pharmaceutical efficacy.

The methods of this invention, generally speaking, may be practiced using any mode of administration that is medically acceptable, meaning any mode that produces effective levels of the active compounds without causing clinically unacceptable adverse effects. Such modes of administration include oral, rectal, topical, nasal, transdermal or parenteral routes. The term "parenteral" includes subcutaneous, intravenous, intramuscular, or infusion. Intravenous and intramuscular routes are not particularly suited for long term therapy and prophylaxis. They could, however, be preferred in emergency situations. Topical administration is preferred because of the convenience to the patient as well as the dosing schedule. Suitable formulations may be found in Remington's Pharmaceutical Sciences.

The compositions containing imidazoles conveniently may be presented in unit dosage form and may be prepared by any of the methods well known in the art of pharmacy. Such methods include the step of bringing the active ingredient into association with a carrier which constitutes one or more accessory ingredients. In general, the compositions are prepared by uniformly and intimately bringing the imidazoles into association with a liquid carrier, a finely divided solid carrier, or both.

The imidazoles useful in the invention may be delivered in a mixture with other anti-proliferation or anti-inflamation drugs. In this embodiment, a common administration vehicle (e.g., topical solution) would contain one or more of the compounds described above as useful in this invention together with the anti-epithelial cell proliferation drug and/or anti-inflamation drug. Thus, the present invention also provides pharmaceutical compositions, for medical use, which comprise the active compounds of the invention together with one or more pharmaceutically acceptable carriers thereof and optionally any other therapeutic ingredients.

Supplementary anti-proliferation drugs and anti-inflamation drugs useful in the invention include: diclofenac; ketoprofen; indomethacin; and acetylsalicylate.

The formulations of the invention are administered in effective amounts. An effective amount is one sufficient to inhibit the proliferation of an epithelial precancerous lesion, thereby effectively inhibiting the growth of the lesion. Effective amounts will depend, of course, on the particular condition being treated; the severity of the condition; lesion size and shape; individual patient parameters including age, and physical condition; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

Generally, daily topical doses of active compounds will be from about 0.2 milligrams/kg per day to 0.7 milligrams/kg per day. In the event that the response in a subject is insufficient at such doses, even higher doses may be employed to the extent that patient tolerance permits. Multiple doses per day are contemplated to achieve effective results.

EXAMPLES

Example 1

Preparation of clotrimazole cream

Six grams of crystalline clotrimazole powder (U.S.P./NF from Spectrum) was added to 184.8 grams of Unibase (Warned Chilcott Laboratories). The solution was mixed to obtain a uniform consistency. 22.2 mL of lactic acid was added to the solution and mixed until a uniform consistency was achieved. Lactic acid was also from Spectrum. Unibase contains purified water, USP; Cetyl alcohol, NF; glycerine USP; Stearyl alcohol, NF; white tetrolatum, USP; Sodium tauryl sulfate, NF; sodium citrate, USP; and propylparaben, NF. The final composition of the cream is clotrimazole, 3% and lactic acid, 5%.

Example 2

Treatment of patients with different proliferative skin conditions with clotrimazole cream Patients having actinic keratosis skin disorders were treated topically with 1 cm$^3$ of a 3% clotrimazole 5% lactic acid cream two times a day on selected lesions. A placebo cream, formulated with the same cream base but without clotrimazole and lactic acid was applied to another set of symmetrical lesions in a double blind fashion. Photographs documenting the lesions were taken before and every three to six weeks after initiation of treatment.

The results showed that in all cases, the cream containing clotrimazole induced an improvement of the dermatological condition. Treatment of the lesions with placebo cream showed no improvement.

Those skilled in the art will be able to ascertain with no more than routine experimentation numerous equivalents to the specific processes and products described herein. Such equivalents are considered to be within the scope of the invention and are intended to be embraced by the following claims.

We claim:

1. A method for treating an epithelial precancerous lesion comprising, administering to a human subject in need of such treatment an effective amount of an imidazole selected from the group consisting of clotrimazole, ketaconazole, econzole, and miconazole, wherein the human subject has an epithelial precancerous lesion selected from the group consisting of actinic keratosis, hypertrophic actinic keratosis, Bowenoid actinic keratosis and radiation keratosis.

2. The method of claim 1, wherein the epithelial precancerous lesion is actinic keratosis.

3. The method of claim 1, wherein the imidazole is clotrimazole.

4. The method of claim 2 wherein the imidazole is clotrimazole.

5. The method of claim 1, wherein said administration is topical.

6. The method of claim 2, wherein said administration is topical.

7. The method of claim 3 wherein the administration is topical.

8. The method of claim 4 wherein the administration is topical.

9. The method of claim 4 wherein the clotrimazole is applied as a 3% clotrimazole topical administration.

10. The method of claim 1, wherein the epithelial precancerous lesion is hypertrophic actinic keratosis.

11. The method of claim 10, wherein the imidazole is clotrimazole.

12. The method of claim 11, wherein the administration is topical.

13. The method of claim 1, wherein the epithelial precancerous lesion is Bowenoid actinic keratosis.

14. The method of claim 13, wherein the imidazole is clotrimazole.

15. The method of claim 14, wherein the administration is topical.

16. The method of claim 1, wherein the epithelial precancerous lesion is radiation keratosis.

17. The method of claim 16, wherein the imidazole is clotrimazole.

18. The method of claim 17, wherein the administration is topical.

19. The method of claim 1, wherein the imidazole is clotrimazole and the clotrimazole is applied as a 3% clotrimazole topical administration.

* * * * *